United States Patent [19]
Kolbly

[11] Patent Number: 5,642,735
[45] Date of Patent: Jul. 1, 1997

[54] TEMPERATURE SENSING DEVICE FOR MEDICAL PATIENTS WITH RELEASABLE HOUSING

[76] Inventor: Kenneth D. Kolbly, 1541 Nancy St., Barstow, Calif. 92312

[21] Appl. No.: 405,222

[22] Filed: Mar. 16, 1995

[51] Int. Cl.$^6$ ............................................. A61B 5/00
[52] U.S. Cl. ............................. 128/736; 128/725
[58] Field of Search .................................. 128/723, 724, 128/725, 726, 736, 666, 671, 687, 734

[56] References Cited

U.S. PATENT DOCUMENTS

| | | | |
|---|---|---|---|
| 3,884,219 | 5/1975 | Richardson et al. | 128/2 R |
| 3,962,917 | 6/1976 | Terada | 128/725 |
| 3,999,537 | 12/1976 | Noiles | 128/2 R |
| 4,222,391 | 9/1980 | Rawson et al. | 128/736 |
| 4,510,941 | 4/1985 | Semrow et al. | 128/671 |
| 4,651,746 | 3/1987 | Wall | 128/671 |
| 5,186,047 | 2/1993 | Gordon et al. | 128/736 |
| 5,211,479 | 5/1993 | Coffeu et al. | 374/151 |
| 5,383,470 | 1/1995 | Kolbly | 128/725 |

*Primary Examiner*—Sam Rimell
*Assistant Examiner*—Pamela Wingood

[57] ABSTRACT

The invention is a portable device for measuring the temperature and respiration rate of a patient. In detail, the device includes a temperature sensing device comprising a housing having first and second ends with an aperture extending there through, and the first end of the housing adapted for insertion into the mouth of the patient. The housing further including a plurality of temperature sensors mounted externally on the second end of the housing. A plurality of electrical contacts are located on the second end of the housing; and a plurality of conductors couple the plurality of temperature sensors to the electrical contacts. A spirometer assembly for measuring the respiration rate of the patient as the patient breathes in and out is included having a second housing with first and second ends and an aperture extending there through. The first end of the spirometer is adapted to releasably engage the second end of the housing of the temperature sensing device. A plurality of second is mounted on the second end of the second housing such that the plurality of first and second contacts are in electrical contact when the second end of the first housing is engaged with the first end thereof. An electrical circuit is included for processing the input temperature signals from the plurality of temperature sensors and providing an output signal proportional thereto to a display device for displaying the temperature of the patent upon receipt of the output signal. While the spirometer in combination with the temperature sensor is an important aspect of the invention, the temperature sensor could be used with a simple hollow tube incorporating the second electrical contacts, electrical circuit and the display device.

9 Claims, 3 Drawing Sheets

TEMPERATURE SENSING DEVICE FOR MEDICAL PATIENTS WITH RELEASABLE HOUSING

BACKGROUND OF THE INVENTION

1. Field of the Invention

The invention relates to the field of medical sensors and, in particular, to the field of temperature sensors for patients combined with a spirometer.

2. Description of Related Art

During emergency treatment of a patient, two of the important physical parameters that the physician must know are the temperature and respiration rate of the patient. In addition, any device or combination of devices must be portable so that it can be used in the field, for example, the seen of an accident. There are numerous portable spirometers available. For example U.S. Pat. No. 5,383,470 "A Portable Spirometer" by K. Kolbly, filed Sep. 30, 1993 (common inventor and assignee) discloses a simple spirometer which allow the patient to breathe there through. Another example can be found in U.S. Pat. No. 3,735,752 "Spirometer" by J. A. Rodder. In both these portable devices one end of the spirometer is inserted into the mouth of the patient who breaths there through and the respiration rate is automatically displayed. There are also numerous electronic type temperature sensors such as disclosed in U.S. Pat. No. 5,211,479 "Digital Pacifier Thermometer" by F. Coffey, et al. This electronic device uses a series of electrical temperature sensors mounted on the end of a child's nipple shaped pacifier. The electronic circuit is capable of comparing the measurement of each temperature sensor and selects the highest stable reading and displays it. However, the patient must breathe through the nose.

There are also numerous devices for simultaneously measuring the respiration rate and temperature of the patient. For example U.S. Pat. No. 3,884,219 "System For Determining Temperature And Respiration Rate" by P. C. Richardson, et al. and U.S. Pat. No. 4,222,391 "Unitary Disposable Sanitary Sheath For Temperature And Respiration Sensing Probe" by P. O. Rawson, et al. In both these devices a housing is included having a hollow tube that is inserted into the mouth. The housing also includes a cup shaped member that is positioned under the nose of the patient to sense respiration rate therethrough. A temperature probe is inserted through the housing and into the mouth to measure temperature. U.S. Pat. No. 3,999,537 "Temperature, Pulse And Respiration Detector" by D. G. Noiles discloses a combination pulse temperature and respiration detector. However, while the temperature and pulse sensors are mounted on a probe that is inserted into the mouth, the respiration rate is measured by sensing air flow from the nose. While these devices will measure both temperature and respiration rate, they do not allow for the simultaneous delivery of oxygen. In addition, if the patient's nasal passageways are closed, due to a cold, respiration rate measurements are not possible.

In U.S. Pat. No. 4,510,941 "Temperature, Pulse And Respiration Mouthpiece Probe" by C. M. Semrow all three measurements are made by probes within the mouth. However, the respiration rate is sensed by a photodetector that operates like a photplethysmograph. That is, it depends upon the photodetector sensing changes in the reflectivity of the interior of the patients mouth that changes with the pulse rate as well as the respiration rate. The same sensor is used to make both readings and electronic circuitry is used to differentiate pulse rate from the slower respiration rate. This device also does not allow for the patient to receive oxygen while taking measurements. In addition, the measuring the reflectivity of the mouth is suspect.

Thus it is a primary object of the invention to provide a temperature sensor that allows patients to breathe through their mouth as the temperature is measured.

It is another primary object of the invention to provide a combination spirometer and temperature sensor.

It is a further object of the invention to provide a combination spirometer and temperature sensor that allows the patient to simultaneously breath through the mouth.

It is a still further object of the invention to provide a combination spirometer and temperature sensor that allows the patient to simultaneously receive oxygen.

SUMMARY OF THE INVENTION

The invention is a portable device for measuring the temperature and respiration rate of a patient. In detail, the device includes a temperature sensing device comprising a housing having first and second ends with an aperture extending there through. The first end of the housing adapted for insertion into the mouth of the patient. The housing further including a plurality of temperature sensors, preferably thermistors, mounted externally on the second end of the housing. A plurality of electrical contacts are located on the second end of the housing; and a plurality of conductors couple the plurality of temperature sensors to the electrical contacts. The housing includes a flange located between the first and second ends thereof that is contoured to fit over the mouth and lips to limit the penetration of the first end of the housing into the mouth. Preferably, the second end includes a bulb like member on or near the second end serves to position the second end behind the teeth of the patient.. Additionally, a flexible fork shaped member extends from the bulb like member with the electrical sensors mounted on the end of the tangs of the fork shaped member. Thus when the second end of the housing is inserted into the mouth, the forked like member is positioned under the tongue, an Ideal location for taking temperature measurements.

A spirometer assembly is included for measuring the respiration rate of the patient as the patient breaths in and out. The spirometer is included having a second housing with first and second ends and an aperture extending there through. The first end of the spirometer is adapted to releasably engage the second end of the housing of the temperature sensing device. A plurality of second contacts are mounted on the second end of the second housing such that the plurality of first and second contacts are in electrical contact when the second end of the first housing is engaged with the first end thereof.

An electrical circuit is included for processing the input temperature signals from the plurality of temperature sensors and providing an output signal proportional thereto to a display device for displaying the temperature of the patent upon receipt of the output signal. The electrical circuit includes a microprocessor for comparing the temperature readings of the temperature sensors and providing a signal proportional to the highest reading. A display device is coupled to the electrical circuit for receiving the signal and visually displaying the temperature.

While it is an important purpose of the invention to integrate the temperature sensor with a spirometer, the temperature sensor's use is not restricted thereto. For example, a simple hollow tube incorporating the electrical circuit and display means could be used in place of the spirometer. However, its use therewith provides a unique combination.

The novel features which are believed to be characteristic of the invention, both as to its organization and method of operation, together with further objects and advantages thereof, will be better understood from the following description in connection with the accompanying drawings in which the presently preferred embodiment of the invention is illustrated by way of example. It is to be expressly understood, however, that the drawings are for purposes of illustration and description only and are not intended as a definition of the limits of the invention.

DESCRIPTION OF THE PREFERRED EMBODIMENT

Figure 1:
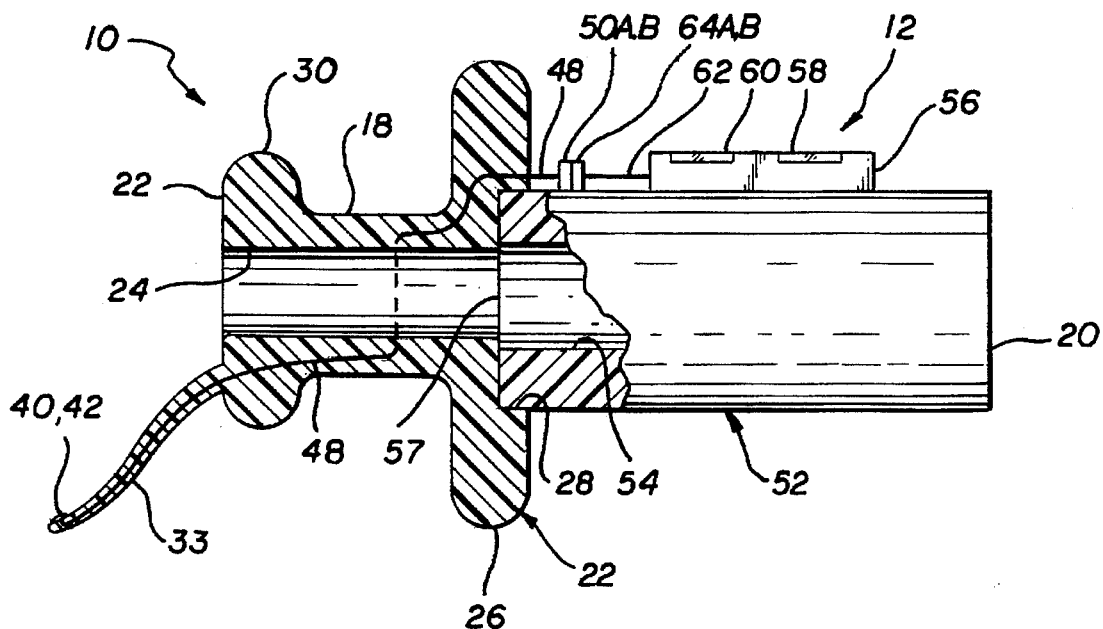
FIG. 1 is a side view of the spirometer and temperature sensing device.
Figure 2:
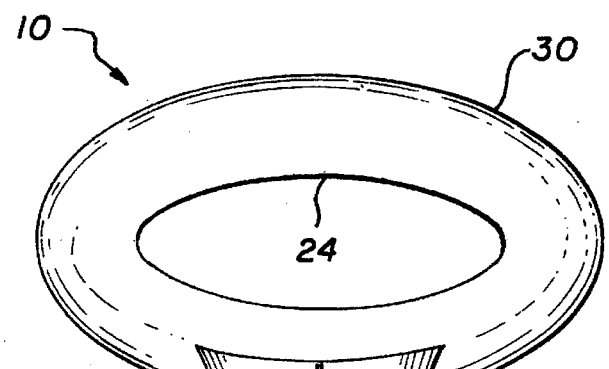
FIG. 2 is a rear view of FIG. 1 illustrating the end of the temperature sensing device.
Figure 3:
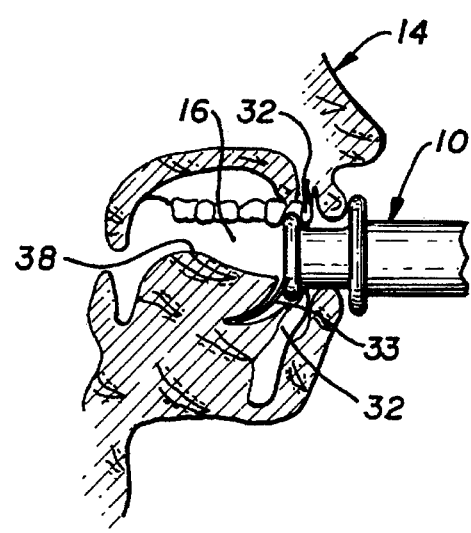
FIG. 3 is a partial cross-sectional side view of a patients mouth with the temperature sensor installed therein.

Illustrated in FIGS. 1 is a temperature sensor assembly, generally indicated by numeral 10 shown joined to a spirometer, generally indicated by numeral 12, while illustrated in FIG. 3 is the joined temperature sensor and spirometer installed in a patient's 14 mouth 16. The temperature sensor assembly 10 includes a hollow tubular housing 18 having a first end 20 and a second end 22 and a passageway 24 there through. The second end 22 of the sensor assembly 10 includes a flange 26, which limits the travel of the sensor assembly into the mouth 16 and includes a counter bore 28. The first end 20 includes a bulb-like member 30 configured to fit behind the teeth 32. Mounted to the member 30 is a flexible fork shaped tab 33 having tangs 34 and 36 that is adapted to fit under the tongue 38 of the patient 14. Temperature sensors 40 and 42 are positioned on the ends of the tangs 34 an 36. While two sensors are shown there, of course, could be more if so desired. The temperature sensors 40 and 42 are connected by wires 44 and 46 which combine together into a cable 48 and pass through the member 30 and across the housing 18 and through the flange 26 and terminate in an electrical connector half 50. The temperature sensor 12 can be made of molded plastic or other similar inexpensive material and the preferred temperature sensors are thermistors, since it is intended that it be disposable.

The spirometer 12 is of the type that includes a housing 52 having an aperture 54 that extends completely there through and incorporates a control and display unit 56 mounted thereon. It is releasably mounted by its end 57 to the counter bore 28. An example of this type of portable spirometer can be found in the previously mentioned patent application to K. Kolbly, herein incorporated by reference. The control and display unit 56 includes a spirometer display 58 and a sensor display 60. An electrical cable 62 contacts the control and display unit 56 to connector half 64 that couples to the connector half 50. Of course other designs having an aperture that allows the patient to breath therethrough can be connected to the temperature sensor 10. In fact, while it is desirable to couple a spirometer to the temperature sensor 12, a simple hollow tube could be used having a control unit just for the temperature sensor 12.

Figure 4:
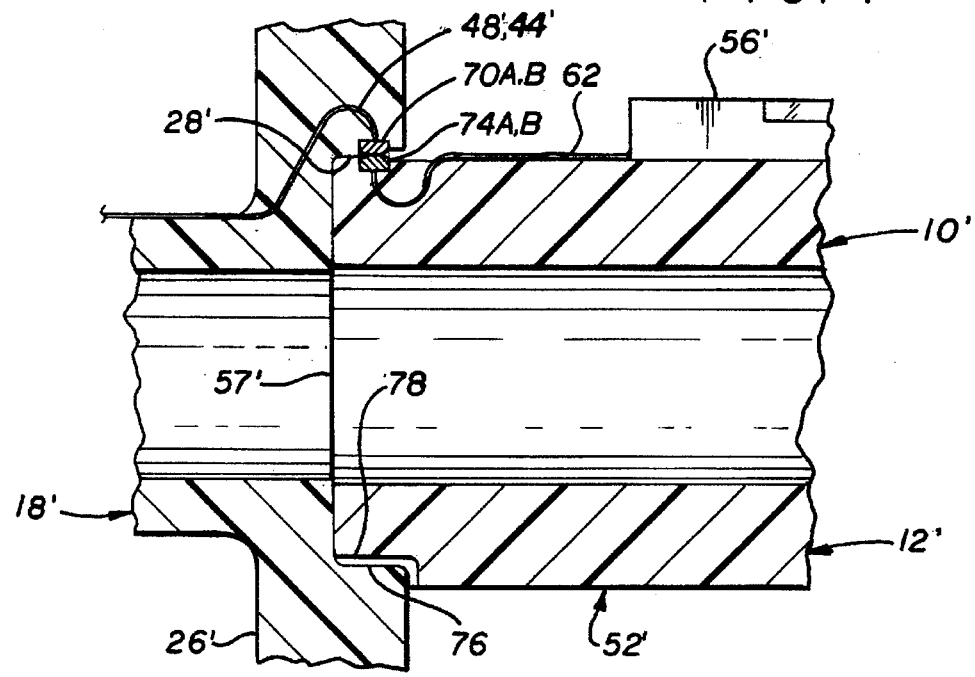
FIG. 4 is a partial side view of spirometer and alternate design for the temperature sensor.

An alternate design for the temperature sensor, now indicated by numeral 10' is illustrated in FIG. 4. Here a cable 48' terminates in contacts 70 on the surface of a counter bore 28'. A cable 62' from a control and display unit 56' on a spirometer 12' terminates in contacts 74 on the end 57' of a housing 52'. Thus when the spirometer 10' is attached to the housing 52' electrical contact is automatically made between contacts 70 and 74. In order to insure that contact is always made, the counter bore 28' incorporates a protrusion 76 that engages a groove 78 on the housing 52', thus assuring proper alignment.

Figure 5:
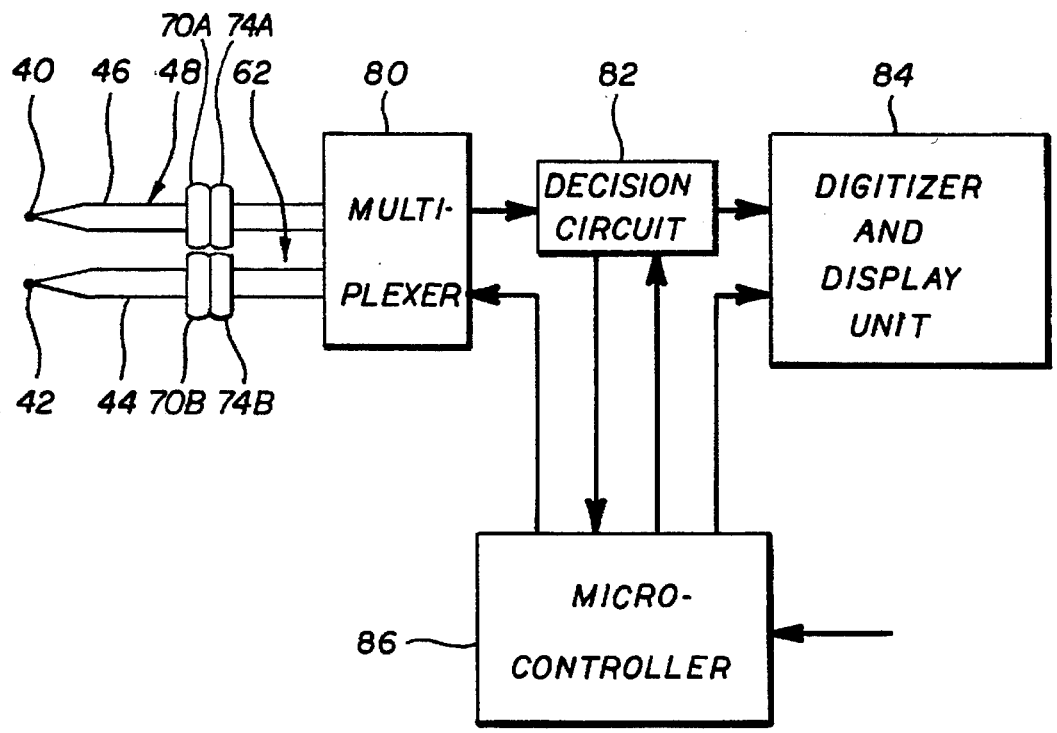
FIG. 5 is a block diagram of the electrical circuit for the temperature sensing device.

A block diagram of the electrical circuit is illustrated in FIG. 5. It can be seen that the signal from the sensors 40 and 42 (for example thermistors) are coupled to a multiplexer 80 which can be commanded to switch from sensor to sensor. A decision circuit 82 receives the output from the multiplexer 80 and converts the thermister changes in resistance to voltages proportional to the temperature and selects the most accurate value. The output from the decision circuit 82 is coupled to a display unit 84. A microcontroller 86 is programmed to control the multiplexer 80 and decision circuit 82 as well as receive input signals from the spirometer 12 and provides output signals to the display unit 84.

Figure 6:
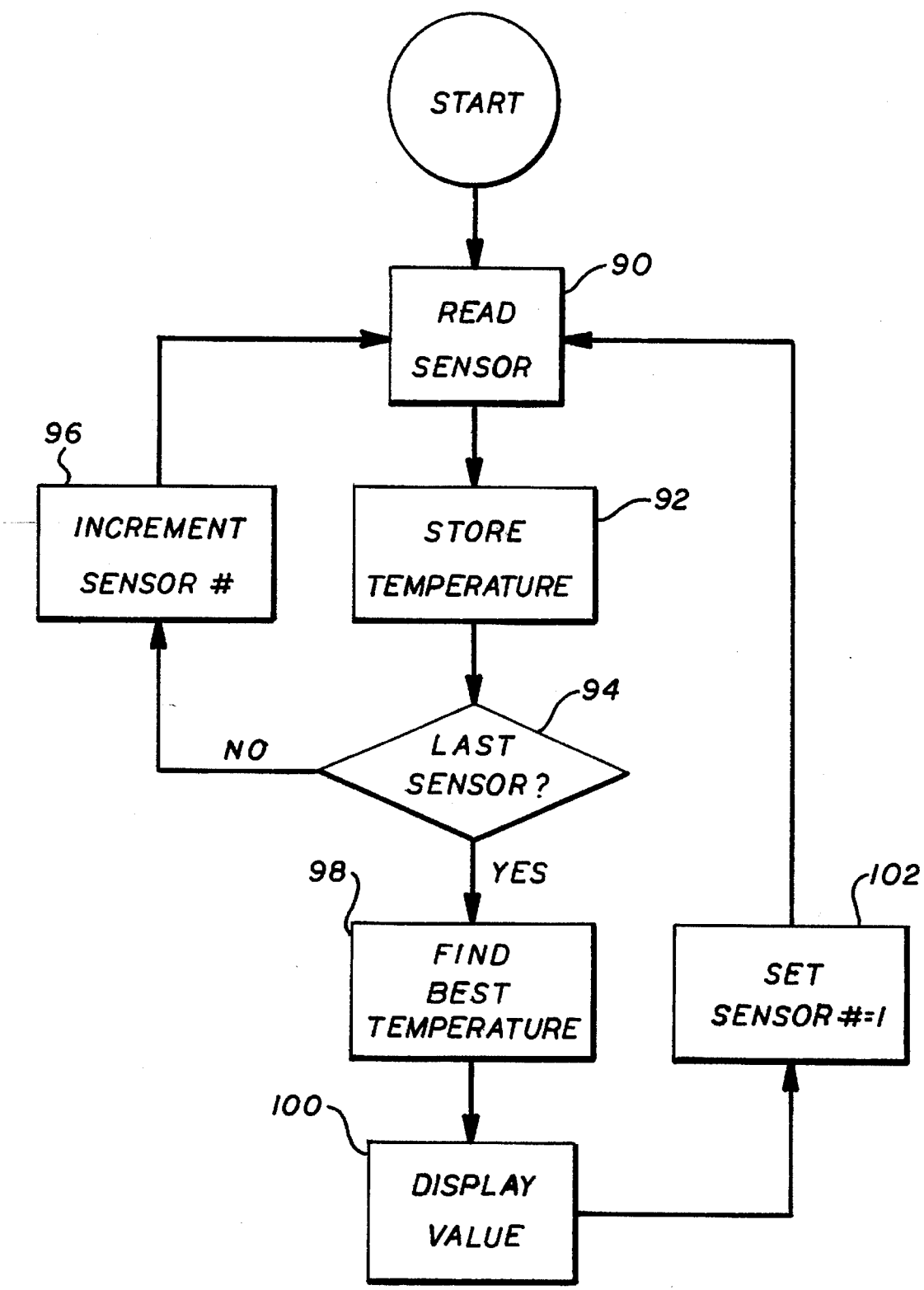
FIG. 6 is a flow chart of the computer program required to analyze the output from the temperature sensors.

Illustrated in FIG. 6 is a flow chart of a computer program that can be utilized by the microcontroller 86.

Step 90—Read the temperature sensor (40 or 42).
Step 92—Store the temperature reading
Step 94—Determine if the last temperature reading is from the last sensor.
Step 96—If no, increment sensor number and go to step 90.
Step 98—If yes, find best temperature.
Step 100—Display value of temperature
Step 102—Reset pointer to first sensor.

With such a flow chart is a simple task to program into the microcontroller.

While the invention has been described with reference to particular embodiments, it should be understood that the embodiments are merely illustrative as there are numerous variations and modifications which may be made by those skilled in the art. Thus, the invention is to be construed as being limited only by the spirit and scope of the appended claims.

INDUSTRIAL APPLICABILITY

The invention has applicability to the medical supply industry.

We claim:

1. A portable device for measuring the temperature of a patient, the device comprising:
   a temperature sensing device comprising:
      a first housing having first and second ends, said first end adapted for insertion into the mouth of the patient, said first housing having an aperture extending from said first end to said second end,
      a plurality of temperature sensors mounted externally on said first end of said first housing;
   a hollow tubular member comprising:
      a second housing having first and second ends, and an aperture extending there through, said first end of said second housing adapted to releasably engage said second end of said first housing, and
      first electrical circuit means for processing the input temperature signals from said plurality of temperature sensors and providing an output signal proportional thereto; and display means for displaying the temperature of the patient upon receipt of said output signal; and second electrical circuit means for electrically coupling said plurality of temperature sensors to said electrical circuit means, said second electrical circuit means having means to electrically disconnect said plurality of temperature sensors from said first electrical circuit means upon disengagement of said first and second housings.

2. The device as set forth in claim 1 wherein said temperature sensor further comprising said second end including a bulb like member adapted to fit behind the teeth of the patient.

3. The device as set forth in claim 2 wherein said temperature sensor comprises:

a flexible member having a forked end having plurality of tangs mounted on said second end of said first housing, said flexible member adapted to fit under the tongue of the patient; and said temperature sensors mounted on the end of said tangs.

4. The device as set forth in claim 3 wherein said temperature sensor comprises a flange mounted on said first housing extending there about between said first and second ends thereof, said flange adapted to limit the travel of said second end of said first mentioned housing into the mouth of the patient.

5. The device as set forth in claim 1, or 2, or 3, or 4 wherein said tubular member is a spirometer having means for measuring and displaying the respiration rate of the patient as said patient breathes in and out.

6. A portable device for measuring the temperature and respiration rate of a patient, the device comprising:

a temperature sensing device comprising:

a first housing having first and second ends, said first end adapted for insertion Into the mouth of the patient, said first housing having an aperture extending from said first end to said second end, and a plurality of temperature sensors mounted externally on said second end of said first housing; and a spirometer assembly comprising:

a second housing having first and second ends, and an aperture extending there through, said first end of said spirometer adapted to releasably engage said second end of said first housing, and means for measuring the respiration rate of the patient as said patient breathes in and out; and electrical circuit means for processing the input temperature signals from said plurality of temperature sensors and providing an output signal proportional thereto;

display means for displaying the temperature of the patent upon receipt of said output signal and;

second electrical circuit means for electrically coupling said plurality of temperature sensors to said electrical circuit means, said second electrical circuit means having means to electrically disconnect said plurality of temperature sensors from said first electrical circuit means upon disengagement of said first and second housings.

7. The device as set forth in claim 6 wherein said temperature sensor further comprising said second end including a bulb like member adapted to fit behind the teeth of the patient.

8. The device as set forth in claim 7 wherein said temperature sensor comprises:

a flexible member having a forked end having plurality of tangs mounted on said second end of said first housing, said flexible member adapted to fit under the tongue of the patient; and said temperature sensors mounted on the end of said tangs.

9. The device as set forth in claim 8 wherein said temperature sensor comprises a flange mounted on said first housing extending there about between said first and second ends thereof, said flange adapted to limit the travel of said second end of said first housing into the mouth of the patient.

* * * * *